(12) United States Patent
Zhang et al.

(10) Patent No.: US 9,129,361 B2
(45) Date of Patent: Sep. 8, 2015

(54) VISUAL INDEXING SYSTEM FOR MEDICAL DIAGNOSTIC DATA

(76) Inventors: Jianguo Zhang, Shanghai (CN); Wenjie Dong, Shanghai (CN); Weiling Zheng, Shanghai (CN); Jianyong Sun, Shanghai (CN)

( * ) Notice: Subject to any disclaimer, the term of this patent is extended or adjusted under 35 U.S.C. 154(b) by 0 days.

(21) Appl. No.: 13/816,660

(22) PCT Filed: Nov. 28, 2011

(86) PCT No.: PCT/CA2011/001304
§ 371 (c)(1),
(2), (4) Date: Jun. 5, 2013

(87) PCT Pub. No.: WO2012/159190
PCT Pub. Date: Nov. 29, 2012

(65) Prior Publication Data
US 2013/0294664 A1 Nov. 7, 2013

(30) Foreign Application Priority Data
May 24, 2011 (CN) .......................... 2011 1 0135658

(51) Int. Cl.
| G06K 9/00 | (2006.01) |
| G06Q 10/00 | (2012.01) |
| G06T 7/00 | (2006.01) |
| A61B 5/00 | (2006.01) |
| G06F 19/00 | (2011.01) |
| A61B 6/00 | (2006.01) |

(52) U.S. Cl.
CPC ............. *G06T 7/0012* (2013.01); *A61B 5/0013* (2013.01); *A61B 6/468* (2013.01); *A61B 6/56* (2013.01); *G06F 19/321* (2013.01)

(58) Field of Classification Search
None
See application file for complete search history.

(56) References Cited

U.S. PATENT DOCUMENTS

| 5,615,112 A | * | 3/1997 | Liu Sheng et al. ..................... 1/1 |
| 5,807,256 A | * | 9/1998 | Taguchi et al. ............... 600/425 |
| 6,055,494 A | * | 4/2000 | Friedman .......................... 704/9 |
| 6,684,188 B1 | * | 1/2004 | Mitchell et al. ................... 705/3 |
| 7,453,472 B2 | * | 11/2008 | Goede et al. .................. 345/634 |
| 7,613,621 B2 | * | 11/2009 | Brown .............................. 705/2 |

(Continued)

FOREIGN PATENT DOCUMENTS

WO   WO 2008/084330   7/2008

OTHER PUBLICATIONS

Dong et al., "Visualization Index for Image-Enabled Medical Records," Medical Imaging 2011: Advanced PACS-based Imaging Informatics and Therapeutic Applications, Proc. of SPIE vol. 7967, 7970Y, 2011.

*Primary Examiner* — Wenpeng Chen
(74) *Attorney, Agent, or Firm* — Kagan Binder, PLLC.

(57) ABSTRACT

The present invention is a system and method for visually indexing medical data about a patient by generating an image for presentation to a user depicting a subset of the patient's body parts, with body parts having associated diagnostic data highlighted. A user may then select a highlighted body part and be presented with some or all of the associated diagnostic data. The user may manipulate the presented image, which is derived from a three dimensional model, to rotate it or zoom is to expose more body parts, or more detailed body parts depicting child body parts associated with the diagnostic data. The system or method may employ a patient index comprising a hierarchical graph with nodes corresponding to body parts and associated with diagnostic data for those body parts.

36 Claims, 4 Drawing Sheets

(56) References Cited

U.S. PATENT DOCUMENTS

| | | | |
|---|---|---|---|
| 2001/0041992 A1* | 11/2001 | Lewis et al. | 705/3 |
| 2002/0169771 A1* | 11/2002 | Melmon et al. | 707/5 |
| 2002/0170565 A1* | 11/2002 | Walker et al. | 128/920 |
| 2003/0140063 A1* | 7/2003 | Pizzorno et al. | 707/104.1 |
| 2004/0037454 A1* | 2/2004 | Ozawa et al. | 382/128 |
| 2004/0078215 A1* | 4/2004 | Dahlin et al. | 705/2 |
| 2005/0033142 A1* | 2/2005 | Madden et al. | 600/407 |
| 2005/0059876 A1* | 3/2005 | Krishnan et al. | 600/407 |
| 2005/0120020 A1* | 6/2005 | Carus et al. | 707/6 |
| 2005/0285853 A1* | 12/2005 | Morita et al. | 345/419 |
| 2005/0289199 A1* | 12/2005 | Aphinyanaphongs et al. | 707/205 |
| 2006/0173858 A1* | 8/2006 | Cantlin et al. | 707/10 |
| 2007/0076931 A1* | 4/2007 | Haider et al. | 382/128 |
| 2007/0106535 A1* | 5/2007 | Matsunaga | 705/3 |
| 2007/0118399 A1* | 5/2007 | Avinash et al. | 705/2 |
| 2008/0195600 A1* | 8/2008 | Deakter | 707/5 |
| 2008/0243550 A1* | 10/2008 | Yao | 705/3 |
| 2008/0273774 A1* | 11/2008 | Mikhail et al. | 382/128 |
| 2009/0054755 A1* | 2/2009 | Shiibashi | 600/407 |
| 2009/0083072 A1* | 3/2009 | Osawa et al. | 705/2 |
| 2009/0164474 A1* | 6/2009 | Noumeir | 707/10 |
| 2009/0177495 A1* | 7/2009 | Abousy et al. | 705/3 |
| 2009/0221880 A1* | 9/2009 | Soderberg et al. | 600/300 |
| 2009/0228299 A1* | 9/2009 | Kangarloo et al. | 705/2 |
| 2010/0082699 A1* | 4/2010 | Miyasa et al. | 707/802 |
| 2010/0121156 A1* | 5/2010 | Yoo | 600/300 |
| 2010/0191541 A1* | 7/2010 | Prokoski | 705/2 |
| 2011/0082710 A1* | 4/2011 | Subash et al. | 705/3 |
| 2011/0145693 A1* | 6/2011 | Mutic et al. | 715/233 |
| 2011/0231205 A1* | 9/2011 | Letts | 705/3 |
| 2011/0238446 A1* | 9/2011 | Chaudhry | 705/3 |
| 2011/0270123 A1* | 11/2011 | Reiner | 600/558 |
| 2012/0197657 A1* | 8/2012 | Prodanovic | 705/2 |
| 2014/0126770 A1* | 5/2014 | Odessky et al. | 382/103 |

* cited by examiner

VISUAL INDEXING SYSTEM FOR MEDICAL DIAGNOSTIC DATA

RELATED APPLICATION

This application claims the benefit from International Application No. PCT/CA2011/001304, filed Nov. 28, 2011, which in turn claims priority from Chinese Application having serial number 201110135658.X, filed on May 24, 2011, both of which are incorporated herein by reference in their entireties.

FIELD OF THE INVENTION

The present invention relates generally to medical information indexing, and more particularly to medical information indexing using a visual index.

BACKGROUND OF THE INVENTION

Medical tests are routinely performed on patients for purposes such as the detection and analysis of disease conditions and monitoring of disease progression. Such medical tests include lab tests, diagnostic examinations by a physician or other medical practitioner, such as a veterinarian, and diagnostic images of a patient's body parts and associated measurements, among other things.

Lab tests generally involve the analysis of the patient's bodily fluids or tissue, which may be removed by a biopsy or other means. Such tests generally result in a report analyzing the fluid or tissue, which may contain, for example, a number of quantitative measurements stated in the form of a report. Such a report may also indicate normal ranges for such measurements for the overall population or for a segment of the population to which the patient belongs (such as males aged 20-29). Reports may be entered and stored in a laboratory information system (LIS) in electronic form and include patient identifying information such as the patient's name and a unique ID code or number used to identify the patient. A medical practitioner may review the lab test report and generate a further report stating any conclusion about disease or other abnormal conditions evidenced by the lab test. Such findings, including any diagnoses or determinations of medical conditions, may be entered into an associated diagnostic report.

A diagnostic examination by a medical practitioner may involve the use of various medical instruments, such as a stethoscope, otoscope or microscope, and result in a written diagnostic report stating the observed or measured results, including quantitative measurements, such as blood pressure. A diagnostic report may include conclusions, or diagnoses, as to whether any abnormal conditions or diseases may be indicated by the results. A diagnostic examination of biopsied tissue may result in a pathology report, which is one type of diagnostic report.

Medical images of a patient's body are generally taken by a technician using an imaging modality, such as an x-ray machine or a magnetic resonance imaging device. At a single imaging session, one or more diagnostic images of one or more body parts may be taken and recorded. Such diagnostic images may then be printed and provided to a medical practitioner directly, or entered into a picture archiving and communication system (PACS) for later access by a medical practitioner. A medical practitioner, such as a radiologist, will generally then review the diagnostic images, possibly in conjunction with prior related diagnostic images and/or test reports, and produce a diagnostic report.

In general, the resulting diagnostic reports containing patient identifying information and the date(s) of the test may also be entered into a medical information system (MIS), such as a radiology information system (RIS), a LIS, an Electronic Medical Record system (EMR), a Electronic Health Record system (EHR) or a Personal Health Record system (PHR), in electronic form as electronic medical records. In general, each test, and the associated reports, may include words and/or one or more codes that indicate the examination type (such as MRI images), the body part(s) examined or affected (e.g. lingual of left lung), numerical data that reflect analysis, and a diagnosis indicating a medical condition or pathological entity (e.g. primary adenocarcinoma).

Multiple tests may be performed on a single patient resulting in various diagnostic images and test reports related to multiple body parts, possibly including multiple diagnostic images and test reports for the same body part performed at the same or different times. The diagnostic images and reports may be stored in multiple computer systems. The resulting volume and location(s) of the information recorded for a patient can make it difficult for a medical practitioner to efficiently review a patient's history and identify all relevant conditions that have been diagnosed without missing any significant findings. The nature of the information also makes it very difficult or impossible for the patient to review and understand the meaning of the test results.

SUMMARY OF THE INVENTION

It is an object of the invention to provide a means for indexing diagnostic data, including multiple diagnostic images and reports, in a manner that makes the information readily accessible to medical practitioners and patients. It is also an object of the invention to present the index of information so as to highlight body parts having associated medical conditions indicated by the diagnostic data in a manner that makes the existence of such medical conditions apparent to a medical practitioner, and allows the associated diagnostic data to be easily accessed by the medical practitioner.

The present invention provides a medical data indexing system comprising software for running on at least one computer processor, the software being adapted to:

a. retrieve from one or more medical information systems, patient records for a plurality of patients, each patient having a set of body parts, the patient record for each patient comprising a specification of one or more target body parts and diagnostic data associated with each of the target body parts;

b. for a specified patient, generate an index image depicting a set of the patient's body parts and, if one of more of the target body parts are depicted in the index image, highlight the depicted target body parts in the index image;

c. receive a data retrieval request from a requestor, the request specifying a patient, and provide the index image for the specified patient to the requestor; and d. if one or more target body parts are highlighted in the index image, and the requestor selects one of the highlighted target body parts, provide some or all of the diagnostic data associated with the selected target body part to the requestor.

The patient's body parts may be depicted in the index image in relative positions corresponding to the relative positions of the body parts in the patient.

The index image may be derived from a three dimensional model of a body.

The index image may depict one or more internal body parts.

The system may allow the requestor to request rotation of the body depicted in the index image, the system may then modify the index image to reflect the requested rotation, and the system may then provide the modified index image to the requestor.

The index image may depict one or more target body parts, the system may allow the requestor to request zooming of the index image to depict one or more of the target body parts so that they occupy a larger area in the zoomed index image than in the index image and so that they are shown with greater detail, the system may zoom the index image accordingly, and the system may provide the zoomed index image to the requestor.

The target body parts may comprise child body parts, and the highlighting of each target body part in the zoomed index image may be limited to the one or more child body parts of the target body part that are associated with the diagnostic data.

The software may be further adapted to analyze the patient record to determine the target body part.

At least one target body part may be depicted and highlighted in the index image.

The patient record may further comprise one or more diagnostic data record specifications for each target body part that specify the type of associated diagnostic data that is available, and the software may be further adapted to provide some or all of the diagnostic data record specifications for one of the target body parts to the requestor if the requestor selects that target body part.

The diagnostic data associated with one or more affected target body parts may specify the existence of a medical condition associated with the one or more affected target body parts, the software may be further adapted to analyze the associated diagnostic data to determine the medical condition, and the affected target body parts depicted in the index image may be highlighted in a manner differentiating them from other body parts.

If an affected target body part is selected by the requestor, the system may provide the requestor with a portion of the associated diagnostic data that contains information used by the software to determine the medical condition.

The analysis of the diagnostic data may be done using natural language processing.

The medical information system may comprise a picture archiving and communication system, one or more of the diagnostic data record specifications may further comprise one or more diagnostic image identifiers associated with one or more of the target body parts, each diagnostic image identifier uniquely identifying a diagnostic image stored by the picture archiving and communication system, and, if the requestor selects a diagnostic data record specification that includes one or more diagnostic image identifiers, the system may provide the requestor with the option of receiving one or more of the diagnostic images identified by one or more of the diagnostic image identifiers.

The medical information system may comprise a laboratory information system, one or more of the diagnostic data record specifications may comprise one or more lab report identifiers, and, if the requestor selects a diagnostic data record specification that includes one or more lab report identifiers, the system may provide the requestor with the option of receiving one or more of the lab reports identified by one or more of the lab report identifiers.

For each target body part, the software may be further adapted to analyze the diagnostic data associated with the target body part to determine a status of the target body part specifying whether, for that target body part, (a) a medical condition exists, (b) a medical condition does not exist, or (c) the software cannot determine whether a medical condition exists, and each target body part depicted in the index image may be highlighted in a manner differentiating whether the target body part's status is (a), (b) or (c).

The patient may be human, the patient record may include the patient's gender, and the generated index image may be based on a three dimensional model of either a man's body or a woman's body, corresponding to the patient's gender.

The patient record, including all available diagnostic data, may be retrieved from the medical information systems immediately after the requestor requests data for the patient.

The requester may be a user, providing the index image may comprise displaying the index image to the user, the user may select a body part using a mouse or touch screen, and providing the associated diagnostic data may comprise displaying some or all of the associated diagnostic data.

The requester may be a client computer process, providing the index image may comprise sending the index image or a pointer to the index image to the client, the client may select a body part by sending a message to the system specifying the body part, and providing the associated diagnostic data may comprise sending the associated diagnostic data or a pointer to the associated diagnostic data to the client.

The patient record provided by the medical data indexing systems may comprise a directed acyclic graph having nodes and edges, wherein the nodes correspond to pre-defined body part identifiers, the edges connect nodes that share a parent-child relationship, and each node corresponding to one of the target data parts is associated with the diagnostic data for that target data part.

The medical data indexing system may comprising a patient indexing server adapted to:
  a. obtain information about a plurality of patients, each patient having a set of body parts, from one or more medical information systems, the information for each patient comprising a specification of one or more target body parts and diagnostic data for each target body part;
  b. for each patient, construct and store a patient index comprising a pre-defined set of body part identifiers by identifying one or more pre-defined body part identifiers corresponding to the specification of each of the target body parts, and associating the diagnostic data for each of the target body parts with the identified pre-defined target body part identifiers in the patient index; and
  c. receive data retrieval requests from requestors, each request specifying a patient, and, for each request, provide the patient index corresponding to the specified patient to the requestor.

In this case, the requestor may be a patient visualization server, the patient visualization server being adapted to:
  a. receive an index image request from a client specifying a patient;
  b. send a data retrieval request to the patient indexing server to request a patient index for the specified patient, and receive the patient index for the specified patient from the patient indexing server;
  c. generate an index image depicting the body parts corresponding to a subset of the pre-defined set of body part identifiers in the patient index, and, if one or more target body parts in the patient index are depicted in the index image, highlight a portion of the index image depicting the one or more target body parts; and
  d. send the index image to the client.

The medical data indexing system may further comprising the patient visualization server.

The patient visualization server may be further adapted to:
a. receive index image revision requests from the client, revise the index image according to each request, highlight the target body parts depicted in the revised index images, and provide the revised index images to the client; and
b. receive data retrieval requests from the client, each request specifying one of the target body parts, and, for each request, provide some or all of the diagnostic data associated with the specified target body part to the client.

The body parts may be depicted in the index image in relative positions corresponding to the relative positions of the body parts in the patient.

The pre-defined set of body part identifiers may be hierarchical, based on parent-child relationships between the body parts, and the patient index may comprise a directed acyclic graph having nodes and edges, wherein the nodes correspond to pre-defined body part identifiers, the edges connect nodes that share a parent-child relationship, and each node corresponding to a particular target body part is associated with the diagnostic data for that particular target body part.

The nodes may contain addresses of, or pointers to, the associated diagnostic data.

The directed acyclic graph may be depicted in the index image, and the nodes with associated diagnostic data may be highlighted.

The invention further comprises a method of indexing medical data by a computer system, the method comprising the steps of:
a. receiving a patient identifier specifying a patient from a requestor, the patient having a set of body parts;
b. retrieving from a medical information system a patient record for the patient, the patient record comprising a specification of one or more target body parts and diagnostic data associated with each of the target body parts;
c. generating an index image depicting a set of the patient's body parts;
d. if one or more of the target body parts are depicted in the index image, highlighting those target body parts in the index image;
e. providing the index image to the requestor; and
f. if the requestor selects one of the highlighted target body parts, providing some or all of the associated diagnostic data to the requestor.

The invention further comprises a method of indexing medical data by a computer system, the method comprising the steps of:
a. receiving a data retrieval request from a requestor, the request specifying a patient;
b. obtaining a patient record for the patient, the patient having a set of body parts, from one or more medical information systems, the patient record comprising a specification of one or more target body parts and diagnostic data for each target body part;
c. constructing a patient index comprising a pre-defined set of body part identifiers by identifying one or more pre-defined body part identifiers corresponding to the specification of each of the target body parts, and associating the diagnostic data for each of the target body parts with the identified pre-defined target body part identifiers in the patient index; and
d. providing the patient index to the requestor.

DETAILED DESCRIPTION OF THE INVENTION

Figure 1:
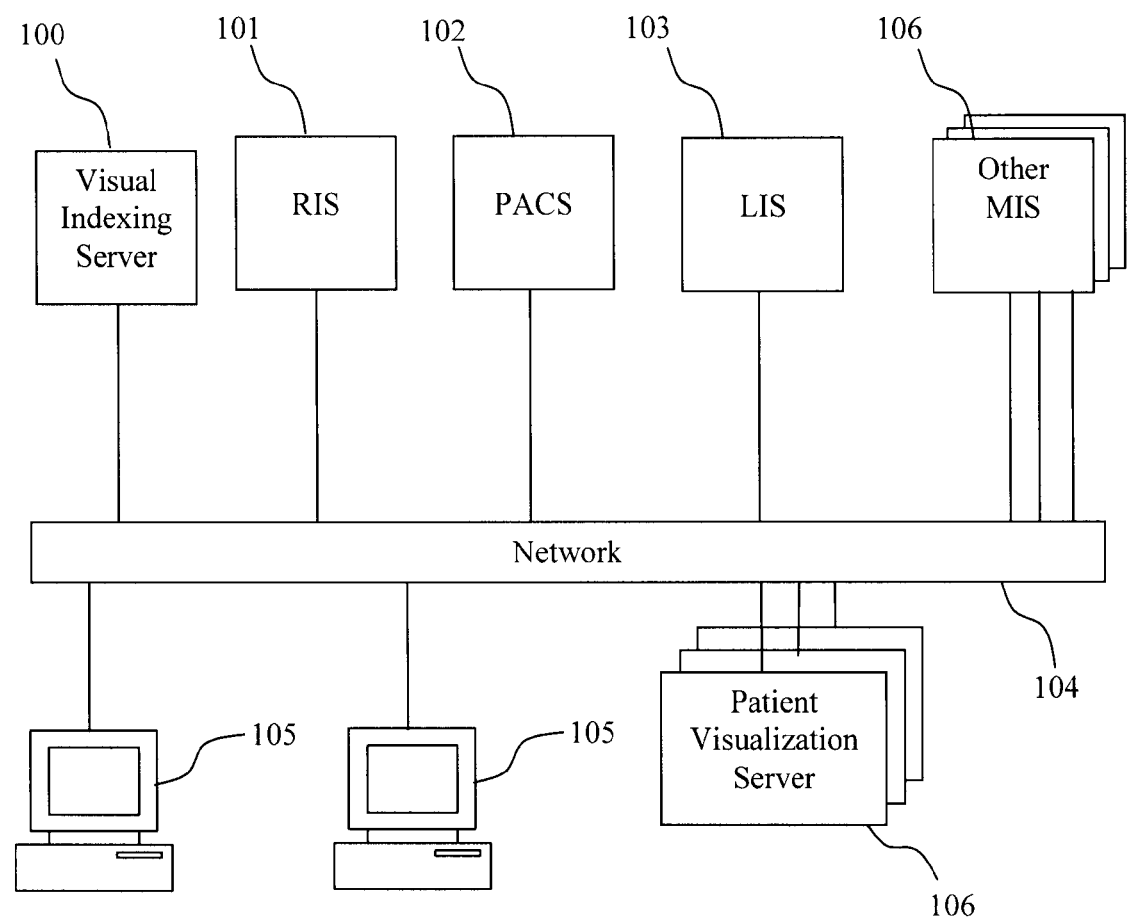
FIG. 1 is a block diagram showing an example of a context in which a visual indexing server and patient visualization server operate.

The context of one embodiment of the invention is shown in FIG. 1, which depicts a visual indexing server (VIS) 100 and a number of patient visualization servers (PVSs) 106 connected via a network 104 to medical information systems (MISs) referred to as a RIS 101, a PACS 102, a LIS 103, and other MISs 106, such as an EMR and an EHR, and also to client systems 105. The VIS 100 may alternatively be referred to as a patient indexing server. In some embodiments, the VIS 100 is an MIS that serves patient indexes to one or more PVSs.

The invention may comprise, for example, (1) a VIS 100, (2) a PVS 106, or (3) a VIS 100 with one or more PVSs 106.

The VIS 100, or in some embodiments the PVS 106, retrieves patient records from the MISs. Each patient record includes patient identifying information (PII), target body part specifications, diagnostic data record specifications (DDRSs, which may also be referred to as metadata), and diagnostic data.

PII may include one or more patient identifiers that uniquely identify the patient, and related information such as the patient's gender, age, address, and, for non-human patients, the type of animal, owner, and trainer.

Target body part specifications are words or codes that identify target body parts for which diagnostic data is available. Such specifications are genrally mapped to an internal coding that associates a unique identifier with each body part, and which may be used in the construction of a patient index as described below. Various differing approaches to specifying body parts in the patient record may be employed. Standardized codes, such as those defined by SNOMED CT™, may be referenced in the record and may be readily interpreted by the system. Where the coding used in the input differs from that used internally, the system must map the codes accordingly, which can be done via look-up tables for example. When unstructured English (or other language) words and phrases are used in the record, the system may employ natural language processing to map such specifications to the internal codes that they most directly correspond to.

A DDRS includes words or codes indicating information about a particular diagnostic session and the information collected at that session. A DDRS generally includes a specification of the type of examination or test performed at the diagnostic session, the date and time of the examination or test, the number of diagnostic images, if any, recorded, and a unique identifier for each image that permits retrieval of the image, and specifications of any associated diagnostic reports, such as a unique identifier for each report, which permits retrieval of the report, and includes information such as the date the report was produced, and, where applicable and available, identification of the person or entity who produced it.

Diagnostic data includes diagnostic images and diagnostic reports, such as lab reports and radiologist reports. Each piece of diagnostic data is generally associated with one DDRS that specifies how to retrieve the diagnostic data and the type of examination or test associated with it.

PVS Embodiments

In a simple embodiment, the system may comprise a single stand-alone PVS, which acts as a medical data indexing system and provides users or client software running on client systems 105 (collectively "requestors") with access to patient records comprising diagnostic data using a visual index in the form of an index image. The index image may be a two-dimensional projection of the three-dimensional (3D) model of a generic human body. The PVS 106 may select a 3D model based on the gender of the patient, which it may determine from PII available on an MIS connected to the network, and then use a male model if the patient is male, or a female model if the patient is female. In the case of an animal, the system may determine the type of animal, such as a dog or a horse, and then select a model for that type of animal to use.

The PVS 106 typically comprises a general purpose computer processor running software adapted to serve requestors with index images and associated patient records, including diagnostic data. If the requestor is a user, the PVS 106 provides a user interface on the user's network attached device 105 and displays index images and associated data from the patient record on the user's network attached device 105.

If the requestor is client software running on a client system, the PVS 106 provides the client software with index images and the patient record, or pointers thereto. A pointer may be, for example, a memory address in a shared memory, or a unique identifier that can be used to query another MIS, such as a PACS, directly to obtain the information or diagnostic image. In such embodiments, the client software is responsible for generating displays containing the index images and diagnostic data.

In the description of these embodiments, it is generally assumed that the PVS 106 displays data directly on the user's network attached device, but it will be evident that the approach described is readily adaptable to work with client software that handles the display and user input.

Patients, which may be human or other animals, are modelled as consisting of a set of body parts. Body parts are generally defined hierarchically via parent-child relationships. For example, a high-level body part might be a head. The head may have a number of child body parts, which are also referred to as body parts, including such parts as a nose, left and right eyes, a cranium, a mandible and a brain. These body parts may also have child body parts. For example, the brain may comprise child body parts including a cerebrum, a cerebellum and a pons, and the cerebrum may further comprise child body parts including a frontal lobe, an occipital lobe, etc. Such body parts may be identified by words, or by codes, in the patient record. Standardized codes may be used, such as those provided by Systematized Nomenclature of Medicine—Clinical Terms (SNOMED CT™), or others such as the American College of Radiology's Index for Radiological Diagnoses (known as the ACR Index) or RadLex™ codes, ICD9, ICD10 or LOINC™, which may vary by the nature of the diagnostic data.

The PVS 106 may obtain patient records directly from MISs, such as a PACS, or it may be adapted to receive patient indexes from a patient indexing server, or VIS, where each patient index comprises a data structure, such as a directed acyclic graph having nodes and edges, where the nodes represent unique pre-defined body part identifiers, each corresponding to a particular body part of the patient, the edges connect nodes representing body parts that share a parent-child relationship, with the direction of each edge going from the parent to the child. Nodes corresponding to certain target data parts are associated with diagnostic data for those target data parts. In general, a "target" body part refers to a body part for which some diagnostic data has been recorded that is available to the system. The root node of the patient index, corresponding to the entire body of the patient, may include PII, such as the patient's name, age and gender and other demographic information.

The set of pre-defined body part identifiers upon which the patient index is based may be selected from a standardized model, such as is provided by SNOMED CT™, which set of body parts may be used internally as the unique pre-defined body part identifiers by the system, and treated as a canonical model. One of the hierarchies defined by SNOMED CT™, which may be suitable is a directed acyclic graph based on parent-child (or "is a") relationships, is "body structure". For example, anatomical structure is a child of body structure, and trunk structure is a child of anatomical structure. These correspond to the whole patient, the patient's anatomy, and the trunk anatomy in the patient index.

Some diagnostic data, such as blood tests or chest x-ray images, may be applicable to multiple body parts at the same level in the patient index. Diagnostic data that focuses on one body part, such as the right eye, is also considered to be associated with the parent body part that includes that body part, such as the head and other ancestor body parts (parent of the parent, etc.). The diagnostic data is generally also associated with one or more child body parts, such as the cornea and lens, and other descendent body parts (children of the children, etc.). Thus each piece of diagnostic data is associated with a sub-graph of body parts of the patient index graph comprising one or more nodes and their connecting edges.

In embodiments not including a separate VIS 100, it will be generally assumed herein that the PVS 106 obtains diagnostic data directly from an MIS, such as a PACS, but the PVS 106 may still construct and cache such patient indexes (and so include the functionality of a VIS) to facilitate rapid access to diagnostic data and rapid generation of index images. Diagnostic data from the MISs may be retrieved and cached as part of the patient index, or the PVS 106 may just associate pointers to the data with the body part nodes in the patient index. Such pointers may be memory addresses in the case of data cached in directly accessible memory, or other unique identifiers than can be used to query the appropriate MIS. In this case, there is no need for the VIS to retain or cache diagnostic data.

In order to determine which body parts particular diagnostic data is available for, the PVS 106 analyzes the patient records. In general, patient records contain specifications of target body parts that the data relates to, either explicitly, via words or codes, or implicitly, e.g. by reference to conditions that are known to be limited to certain body parts, such as a concussion. This may involve scanning diagnostic reports in the patient record for codes indicating particular body parts, or performing natural language processing on reports containing words that specify the associated body parts.

The PVS 106 may periodically poll the available MISs on the network 104 for patient records, some MISs may be configured to push patient records to the PVS 106 as they are added or revised, or a PVS 106 may query MISs upon receipt of a request from a requestor. In general, patients for whom information is available in the MISs are each identified by one or more unique identifiers. The PVS 106 may initially obtain records for all patients from the MISs and construct and store patient indexes in a visual index database, possibly along with some of the associated diagnostic data.

A requestor may provide a patient identifier to the PVS 106 to request diagnostic data about that patient. The PVS 106 may respond by identifying the available diagnostic data, which may be accessible by links stored in a pre-constructed patient index for that patient, or by querying the available MISs for such information. Based on this, the PVS 106 is aware of which target body parts diagnostic information is available for. The PVS 106 may then generate an index image, which it provides to the requestor, e.g. by drawing it on a user's display or by transmitting a pointer to an image, that depicts a set of the patient's body parts. The set of body parts depicted in the index image may include all or a subset of a patient's body parts. Generally a plurality of more than two body parts are depicted in relative positions corresponding to the relative positions of the body parts in the patient. For example, the PVS may initially present a front view depicting body parts including internal organs, blood vessels, lymphatic vessels, muscles, bones and nerves visible from the front, generally in the absence of skin and fat. In some cases, such as where a skin condition is indicated, skin may also be depicted. Depending on the patient, or input from the requestor, the set of depicted body parts may be a restricted subset of the visible body parts, such as the set of body parts including only bones and blood vessels. Body parts that are depicted, but which would otherwise hide other body parts, may be rendered so as to be translucent or transparent in some cases.

Figure 2:
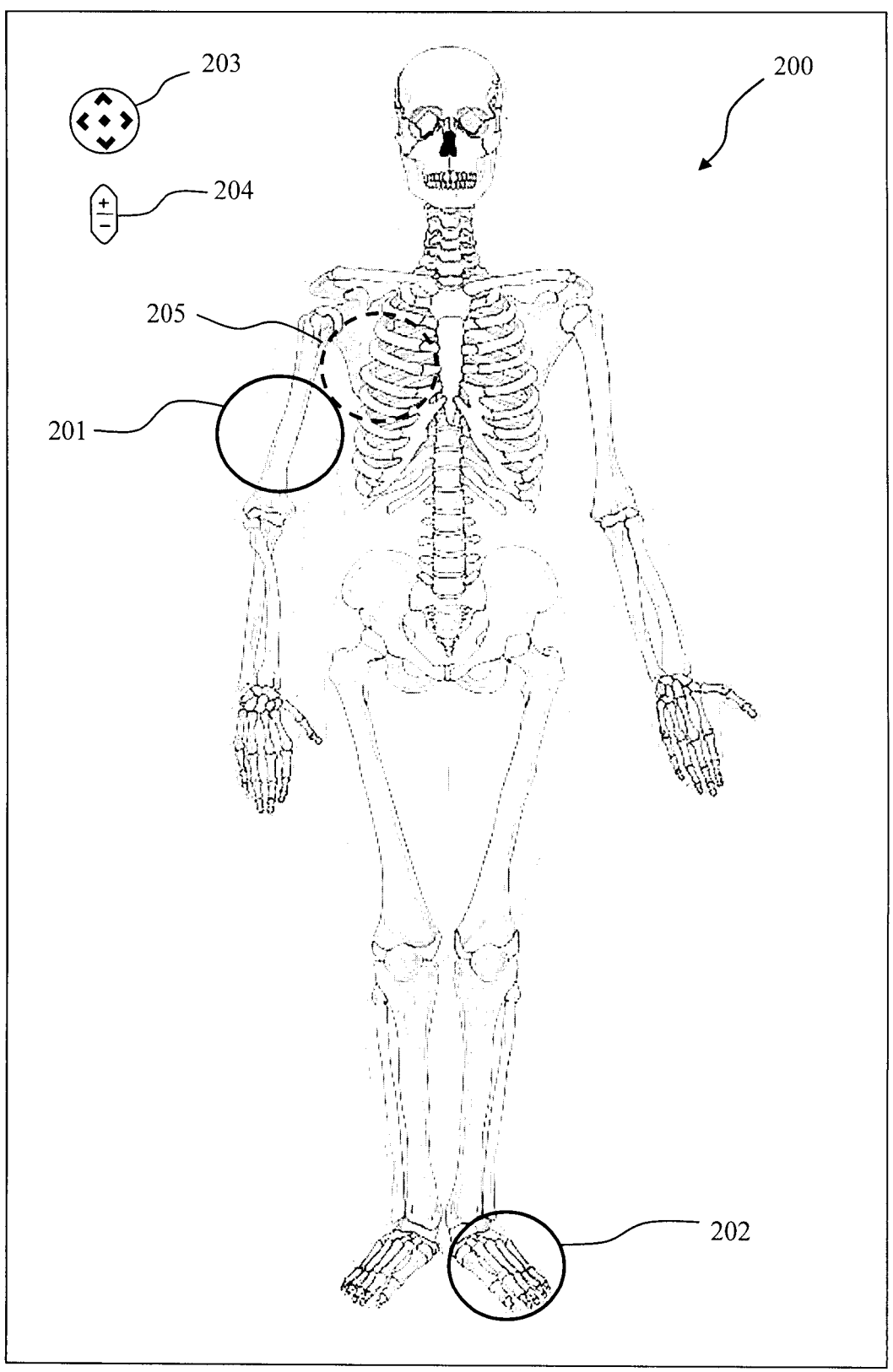
FIG. 2 shows a portion of a display screen showing an index image generated by the system depicting the skeleton of a patient in a front view with three target body parts highlighted in this embodiment by circles.
Figure 3:
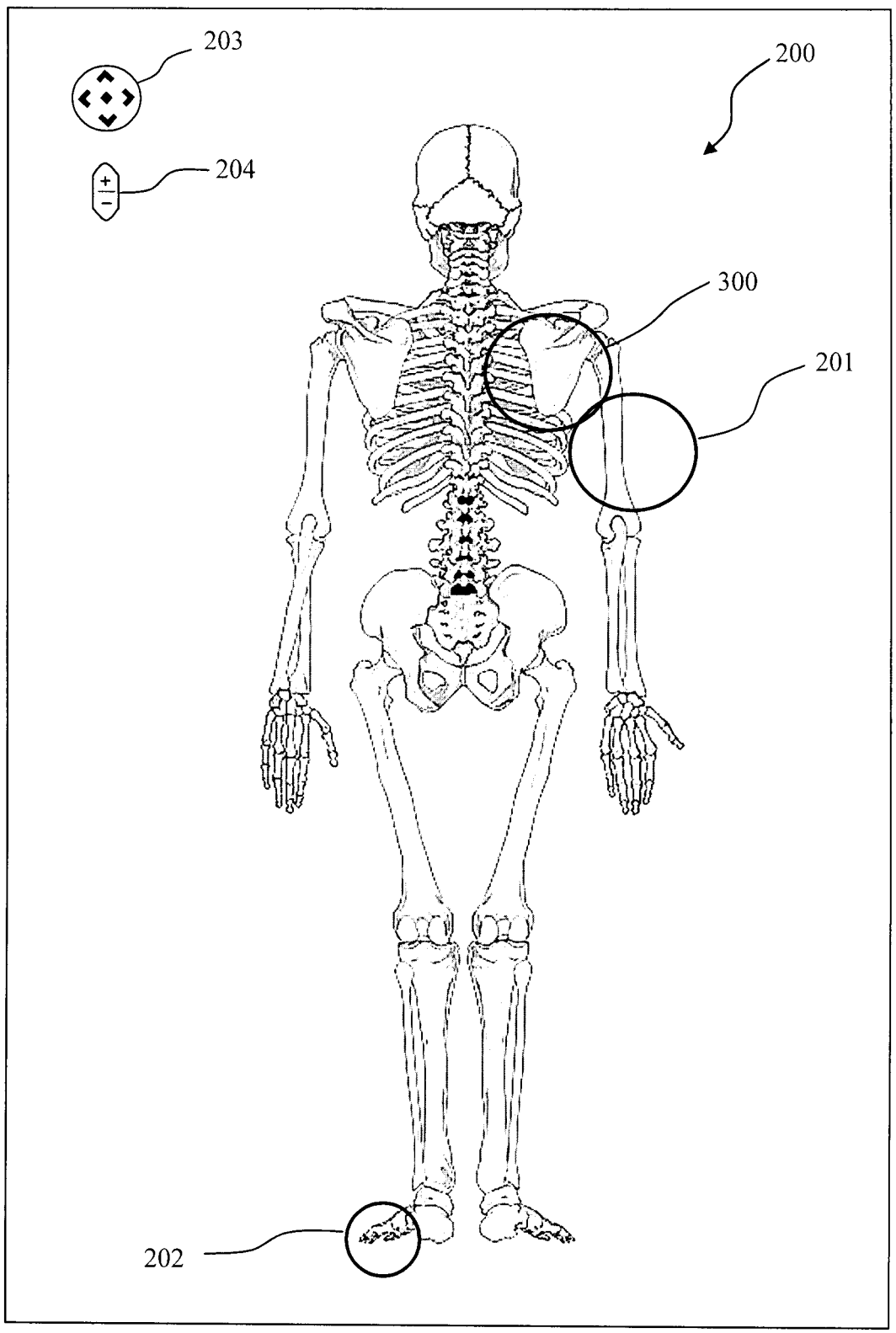
FIG. 3 shows a portion of a display screen showing an index image generated by the system depicting the skeleton of a patient in a rear view with three target body parts highlighted by circles.

An example of such an initial index image of a body 200 is provided in FIG. 2, which is limited to showing bones and an outline of the outer portion of the patient's body. The PVS 106 may then highlight the target body parts for which diagnostic data is available. For example, in the case of FIG. 2, the system has determined that there is diagnostic data available for the right humerus 201, the left foot 202, and the right scapula 205, and has highlighted these body parts by circling them. Highlighting may be done by a solid circle, as shown in FIGS. 2 and 3, colouring or other means for target body parts that are depicted in the current index image that is displayed. For target body parts that are not visible in the current index image, such as the scapula 205 in FIG. 2, other means, such as a broken circle or a tag, may be used to indicate the availability of diagnostic data and distinguish or differentiate them from body parts that have no diagnostic data associated with them.

The PVS 106 software may further analyze the diagnostic data associated with each target body part to determine if the data indicates the existence of a medical condition that deserves or requires the attention of a medical practitioner. A medical condition may be, for example, the existence, or possible existence, of a disease, such as Alzheimer's disease, a symptom or syndrome, such as dementia, or an abnormality, such as amyloid plaques in the cerebral cortex, as identified by a medical practitioner and recorded in the diagnostic data. Abnormalities may include the existence of a pathological entity, such as a tumour or a fibroadenoma. For such pathological entities, the diagnostic data may further indicate whether the entity indicates, or may indicate, a problem, such as a disease. This may be expressed by the use of codes or by words in the diagnostic data, and the PVS 106 may employ natural language processing to determine what, if any, medical conditions, or possible medical conditions, are associated with each target body part. A medical condition may also be the determination by the PVS 106 that a quantitative measurement contained in diagnostic data exceeds or is less than a pre-defined threshold, or is in a particular range of values, where the threshold or range is specified by the medical profession as indicating a medical condition, such as systolic blood pressure exceeding 140 mmHG for an adult human patient, indicating hypertension.

In some cases, the PVS 106 may be able to determine that no medical condition has been identified for certain target body parts. For example, a radiology report may indicate that the associated x-ray images are normal. In other cases, the diagnostic data may indicate the possible presence of a medical condition. For example, a report may include words referring to a "possible abnormality", or a measurement on a lab report may fall within a range specified by the medical profession as being of concern, but not necessarily indicating a medical condition. In such cases, the PVS 106 may classify the target body part as having a possible medical condition. In other cases, there may be no clear indication in the diagnostic data as to whether a medical condition, or possible medical condition, exists that can be identified by the PVS 106 software.

Each body part may thereby be assigned a status by the PVS, the status being, for example, one of: (a) a medical condition, or possible medical condition, exists; (b) a medical condition, or possible medical condition, does not exist; or (c) the PVS 106 software cannot determine whether a medical condition, or possible medical condition, exists. The PVS 106 may then highlight target body parts to differentiate these three states. For example, those with status (a) may be coloured red, those with status (b) coloured yellow, and those with status (c) coloured green. Body parts having no associated diagnostic data would not be coloured.

In general, the existence of a medical condition is primarily associated with a particular body part at a particular level in the body part hierarchy, which is a single node in the patient index. That medical condition is then considered by the PVS 106 to also be associated with all body parts corresponding to all ancestor and descendent nodes of the particular body part in the patient index. For example, a medical condition associated with the frontal lobe of the brain would also be considered to be associated with each of its ancestor body parts, such as the cerebrum, the brain, and the head. In many cases, the medical condition may be associated with a leaf node in the patient index (i.e. a node representing a body part with no child body parts). However, in other cases, particularly before a condition is fully diagnosed, a medical condition may be primarily associated with a non-leaf node. In that case, the PVS 106 will also associate the medical condition with all descendents of the node (i.e. all child body part nodes, children of those children, etc.) In the index image presented to the user then, highlighting will generally be applied to lowest level body parts associated with the medical condition that are distinguishable in that index image. For purposes of highlighting, the severity of medical condition associated with a body part will generally be considered to be the most severe condition associated with any descendant body part.

In the case of the patient depicted in FIG. 2, the diagnostic data may be determined to indicate that the patient has a fractured humerus 201 that requires further treatment, a metatarsal with a stress fracture in the left foot 202 that does not require treatment, and a normal scapula 205. Based on this, the PVS 106 may highlight the humerus 201 in red indicating a serious medical condition, the left foot 202 in yellow indicating a non-serious medical condition, and the scapula 205 in green indicating no medical condition. This immediately draws the user's attention to the red and yellow highlighted target body parts indicating that further treatment or diagnosis of those body parts is required.

The user may then select one of the highlighted body parts, for example, by placing a cursor over the highlighted humerus 201 by using a mouse and clicking on it. The PVS 106 may then display some or all of the associated diagnostic data on the screen near the humerus 201. For example, the PVS 106 may have found DDRSs for two x-ray evaluations, each including pointers to a set of one or more x-ray images with an associated radiologist report, and for one physician's report from a physical examination.

The selection of a body part may be done by any suitable means such as by using a mouse or touch screen interface. Many other approaches are possible such as the use of motion-sensing technology (such as a Wii™ controller, a wired glove or Kinect™).

In general, each kind of diagnostic data has an examination, or test, type specified in the associated DDRS, which may be specified in the diagnostic data by codes or words, and which may be analyzed by the PVS 106 to determine the examination types of the available diagnostic data. After the user selects the highlighted humerus 201, the PVS 106 may then display a list of the three available examination types with associated dates when the associated diagnostic data was created or last modified. These may also be differentially highlighted, e.g. by colour coding, so that, for example, the displayed examination types corresponding to diagnostic data containing the information used to determine that a medical condition exists are coloured red. The user may then be permitted to click on any of the listed types to view the associated diagnostic data. For example, selecting one of the x-ray evaluations may cause to the PVS 106 to display the associated radiology report along with links to the x-ray images. The user may then select any of the image links, causing the PVS 106 to retrieve and display those diagnostic images along with the report.

After being presented with an initial index image, such as that shown in FIG. 2, the user may then decide to rotate the index image in order to show a target body part that is indicated but not depicted in the index image. This may be done using a control such as item 203 in FIG. 2. If the user rotates the index image by 180 degrees, the user may be presented with the revised rotated index image shown in FIG. 3. In this view, the user can clearly see that the right scapula 300 has been highlighted as a target body part having associated diagnostic data.

The PVS 106 may also allow the user to zoom the index image, for example, by selecting a portion such as the left foot 202 and then pressing the "+" in the control 204. In general, when a user zooms the index image, the PVS 106 renders the zoomed portion of the index image in more detail so that the selected target body part occupies a larger area in the zoomed index image than in the previous index image, and some previously indistinguishable child body parts may become distinguishable. In the case of the left foot 202, the PVS 106 may render the foot in more detail and only highlight the metatarsal that has the stress fracture. In some cases, multiple child body parts may have separate diagnostic data associated with them, so that some diagnostic data that was associated with the parent body part is then associated with only one of the child body parts in the zoomed image and other diagnostic data that was associated with the parent body part is then associated with a different child body part in the zoomed image.

It should be noted that the use of a patient index within the PVS 106 is only one means of storing information about body parts of a patient, and its use is not essential. For example, one embodiment of a PVS 106 does not cache such information at all but rather retrieves required information from MISs in real-time in response to user input.

VIS and PVS Embodiments

Figure 4:
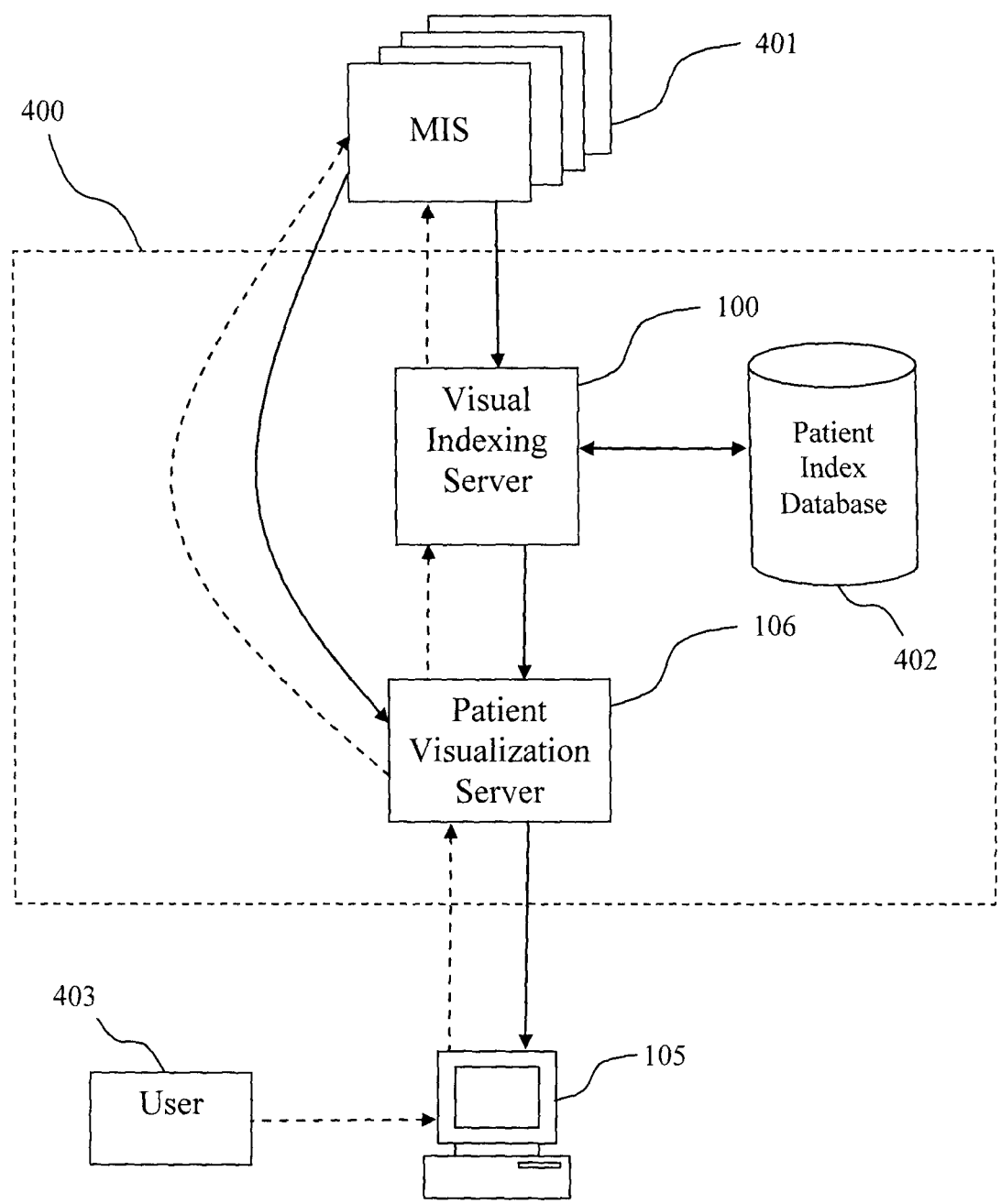
FIG. 4 is a block diagram showing a visual indexing server and patient visualization server and the major data flows.

In other embodiments, the invention 400 may comprise a VIS 100 and one or more separate PVSs, as depicted in FIG. 4. In FIG. 4, arrows depict major data flows, with dashed arrows representing requests for information and solid arrows depict the requested information.

The VIS 100 is generally a general purpose computer processor running server software that acts as a server to a requestor, retrieves patient records from MISs 401, and constructs patent indexes that are stored in a patient index database 402. As described above, each patient index may comprise a data structure, such as a directed acyclic graph having nodes and edges, where the nodes represent pre-defined body part identifiers, each corresponding to a particular body part of the patient, the edges connect nodes representing body parts that share a parent-child relationship, and nodes corresponding to certain target data parts are associated with diagnostic data for those target data parts. The target data part nodes may contain pointers to the associated diagnostic data. Such a pointer may be a memory address in the patient index database 402 or in other network-accessible storage, or it may be an identifier that identifies the MIS that contains the data and a diagnostic data identifier that can be used to query that MIS and retrieve the data.

The requestor shown in FIG. 4 is a PVS 106, which may render and display index images and diagnostic data directly to a user 403, or may serve index images and diagnostic data to client software running on a user's computer system 105, for example.

The PVS 106 receives display requests from a client 105 identifying a patient, generally by providing an identifier, which could be a number, combination of numbers and letters, or possibly the name of the patient. In the latter case, the PVS may identify multiple patients matching the name provided, in which case it may provide a list to the client 105 including other information about each patient, such as gender, age and address, and allow the client 105 to select one patient from the list.

Having identified a single patient, the PVS 106 then sends a data retrieval request to the VIS 100 specifying the patient for whom data is requested. The VIS 100 may then identify a patient index corresponding to that patient in the patient index database 402, and provide the patient index, or a pointer to the patient index, to the PVS 106. If there is no such patient index in the patient index database 402, the VIS 100 may then query the MISs on the network for information on the patient and construct a patient index for that patient. If there is a patient index, the VIS 100 may still query the available MISs to determine if any updated diagnostic data that is not yet linked into the patient index is available.

Having received the patient index, the PVS 106 then renders an initial index image of a body as discussed above and provides it to the client 105. The rendering is done by first selecting an initial view, such as a front view of the full body, and optionally selecting a subset of the body parts to render, such as the skeletal and muscular systems. The system may employ a 3D model of a human body containing all the parts represented in the patient index, where the body parts in the model are located in relative positions corresponding to the positions of the body parts in a patient. Then the two dimensional index image is rendered by performing a two dimensional projection of the model in the selected orientation and including only those body parts that are in the selected subset of body parts visible in the selected view and which can be distinguished at the selected resolution/image size. The depicted body parts therefore correspond to a further subset of the selected subset of body parts. In general, many of the lowest level (or leaf) node body parts associated with visible body parts will not be visible in an index image of the entire patient. These may become visible if the image is zoomed.

Target body parts that are depicted and distinguishable in the index image with associated diagnostic data are highlighted by the PVS 106 in the image, as discussed above. The client then displays the received index image to the user 403 and receives input from the user 403. The user 403 may request that the index image be rotated or zoomed, as discussed above, or otherwise manipulated. The client 105 then formulates an index revision request to request that the PVS 106 perform the requested image manipulation and sends the request to the PVS 106. Upon receipt of an image revision request, the PVS 106 revises the index image accordingly and provides the revised index image to the client 105. In some cases, this may include a number of index images to be displayed in sequence, such as when rotating the index image by a significant amount so that the client 105 can present a smoothly rotating image to the user 403.

The user 403 may also select a target body part, for example by clicking on it using a mouse, in which case the client formulates a data retrieval request and sends it to the PVS 106, identifying the patient and the target body part. Having received such a data retrieval request, the PVS 106 retrieves some or all of the associated diagnostic data associated with the target body part. It may do this by sending a request to the VIS 100, or, if the patient index contains pointers to the data, by directly accessing the data, or sending a request directly to one or more MISs. Having retrieved or otherwise received the diagnostic data, the PVS 106 provides it to the client 105 for display to the user 403. The diagnostic data provided initially to the client 105 may include a list of DDRSs specifying which types of diagnostic data are available, the dates that the data were recorded or last updated and other examination-specific information (such as an examination or record number).

In response to user input, the client 105 may then make additional data retrieval requests, for example to retrieve all the diagnostic images and associated reports associated with a particular diagnostic type with a particular examination number.

Generally, a computer, computer system, client or server includes, as will be well understood by a person skilled in the art, one or more computer processors, and may include separate memory, and one or more input and/or output (I/O) devices (or peripherals) that are in electronic communication with the one or more processor(s). The electronic communication may be facilitated by, for example, one or more busses, or other wired or wireless connections. In the case of multiple processors, the processors may be tightly coupled, e.g. by high-speed busses, or loosely coupled, e.g. by being connected by a wide-area network.

A computer processor, or just "processor", is a hardware device for performing digital computations. A programmable processor is adapted to execute software, which is typically stored in a computer-readable memory. Processors are generally semiconductor based microprocessors, in the form of microchips or chip sets. Processors may alternatively be completely implemented in hardware, with hard-wired functionality, or in a hybrid device, such as field-programmable gate arrays or programmable logic arrays. Processors may be general-purpose or special-purpose off-the-shelf commercial products, or customized application-specific integrated circuits (ASICs).

Computer-readable memory can include any one or a combination of volatile memory elements, such as random access memory (RAM), which may be DRAM, SRAM, SDRAM, etc., and nonvolatile memory elements, such as a ROM, PROM, FPROM, OTP NVM, EPROM, EEPROM, hard disk drive, solid state disk, magnetic tape, CDROM, DVD, etc.). Memory may employ electronic, magnetic, optical, and/or other technologies. Memory may be distributed where at least two components are remote from one another, but are still accessible by one or more processors.

Software may include one or more separate computer programs configured to provide a sequence of instructions to the processors to cause the processors to perform computations, control other devices, receive input, send output, etc.

It should be emphasized that the above-described embodiments of the present invention, particularly, any "preferred" embodiments, are possible examples of implementations, merely set forth for a clear understanding of the principles of the invention. Many variations and modifications may be made to the above-described embodiment(s) of the invention as will be evident to those skilled in the art.

The words "comprises" and "comprising", when used in this specification and the claims, are to used to specify the presence of stated features, elements, integers, steps or components, and do not preclude, nor imply the necessity for, the presence or addition of one or more other features, elements, integers, steps, components or groups thereof.

The scope of the claims that follow is not limited by the embodiments set forth in the description. The claims should be given the broadest purposive construction consistent with the description as a whole.

What is claimed is:

1. A medical data indexing system comprising:
   (a) a programmable computer processor;
   (b) a non-transitory computer-readable memory accessible by the computer processor;
   (c) software stored in the computer-readable memory, wherein when the software is executed by the computer processor, the software causes the computer processor to:
      (i) retrieve from one or more medical information systems, each medical information system being separate and distinct from, and designed and developed separately from, the medical data indexing system, via a computer network, electronic patient records for a plurality of patients, each patient having a set of body parts, the patient record for each patient comprising (1) a specification of one or more target body parts having diagnostic data associated therewith stored in one of the medical information systems, one or more of the target body parts being an affected target body part, each of whose associated diagnostic data indicates the existence of a medical condition associated with the affected target body part, and (2) the diagnostic data associated with each of the target body parts;
      (ii) analyze the patient records to determine which body parts are the target body parts;
      (iii) analyze the diagnostic data to determine which body parts are the affected target body parts and to identify the indicated medical conditions;
      (iv) for a specified patient, generate an index image depicting a set of the patient's body parts, including one or more internal body parts, and, if one or more of the target body parts identified by the medical data indexing system's analysis of one of the patient records retrieved over the computer network from one of the medical information systems are depicted in the index image, automatically highlight the depicted target body parts in the index image, and if one or more affected target body parts are depicted in the index image then, for each depicted affected target body part, automatically highlight the depicted affected target body part in a manner differentiating it from other body parts;

(v) receive a data retrieval request from a requestor, the request specifying a patient, and provide the index image for the specified patient to the requestor; and (vi) if one or more target body parts are highlighted in the index image, and the requestor selects one of the highlighted target body parts, provide some or all of the diagnostic data associated with the selected target body part to the requestor.

2. The medical data indexing system of claim 1 wherein the patient records for at least one patient are retrieved from at least two medical information systems via the computer network and combined by the medical data indexing system.

3. The medical data indexing system of claim 2, wherein the index image is derived from a three dimensional model of a body.

4. The medical data indexing system of claim 3, wherein the system allows the requestor to request rotation of the body depicted in the index image, the system modifies the index image to reflect the requested rotation, and the system provides the modified index image to the requestor.

5. The medical data indexing system of claim 2 wherein the patient records for one patient are retrieved from at least two picture archiving and communication systems.

6. The medical data indexing system of claim 1 wherein the patient's body parts are depicted in the index image in relative positions corresponding to the relative positions of the body parts in the patient.

7. The medical data indexing system of claim 1, wherein (a) the index image depicts one or more target body parts, (b) the system allows the requestor to request zooming of the index image to depict one or more of the target body parts so that they occupy a larger area in the zoomed index image than in the index image and so that they are shown with greater detail, (c) the system zooms the index image accordingly, and (d) the system provides the zoomed index image to the requestor.

8. The medical data indexing system of claim 7, wherein one or more of the target body parts comprise child body parts, and the highlighting of each target body part in the zoomed index image is limited to the one or more child body parts of the target body part that are associated with the diagnostic data.

9. The medical data indexing system of claim 1, wherein the specification of a target body part retrieved over the computer network from one of the medical information systems comprises one or more words and the software further causes the computer processor to analyze the words in the patient record to automatically determine the target body part.

10. The medical data indexing system of claim 9, wherein the analysis of the diagnostic data is done using natural language processing.

11. The medical data indexing system of claim 1, wherein at least one target body part is depicted and automatically highlighted in the index image.

12. The medical data indexing system of claim 1, wherein the patient record further comprises one or more diagnostic data record specifications for each target body part that specify the type of associated diagnostic data that is available, and the software further causes the computer processor to provide some or all of the diagnostic data record specifications for one of the target body parts to the requestor if the requestor selects that target body part.

13. The medical data indexing system of claim 12, wherein the medical information system comprises a picture archiving and communication system, one or more of the diagnostic data record specifications further comprise one or more diagnostic image identifiers associated with one or more of the target body parts, each diagnostic image identifier uniquely identifying a diagnostic image stored by the picture archiving and communication system, and, if the requestor selects a diagnostic data record specification that includes one or more diagnostic image identifiers, the system provides the requestor with the option of receiving one or more of the diagnostic images identified by one or more of the diagnostic image identifiers.

14. The medical data indexing system of claim 12, wherein the medical information system comprises a laboratory information system, one or more of the diagnostic data record specifications comprises one or more lab report identifiers, and, if the requestor selects a diagnostic data record specification that includes one or more lab report identifiers, the system provides the requestor with the option of receiving one or more of the lab reports identified by one or more of the lab report identifiers.

15. The medical indexing system of claim 1, wherein, when one of the affected target body parts is selected by the requester, the system provides the requestor with a portion of the associated diagnostic data that contains information used by the software to determine the medical condition.

16. The medical data indexing system of claim 1, wherein, for each target body part, the software further causes the computer processor to analyze the diagnostic data associated with the target body part to determine a status of the target body part specifying whether, for that target body part, (a) a medical condition exists, (b) a medical condition does not exist, or (c) the software cannot determine whether a medical condition exists, and wherein each target body part depicted in the index image is automatically highlighted in a manner differentiating whether the target body part's status is (a), (b) or (c).

17. The medical data indexing system of claim 1, wherein the patient is human, the patient record includes the patient's gender, and the generated index image is based on a three dimensional model of either a man's body or a woman's body, corresponding to the patient's gender.

18. The medical data indexing system of claim 1, wherein the patient record, including all available diagnostic data, is retrieved from the medical information systems immediately after the requestor requests data for the patient.

19. The medical data indexing system of claim 1, wherein the requester is a user, providing the index image comprises displaying the index image to the user, the user selects a body part using a mouse or touch screen, and providing the associated diagnostic data comprises displaying some or all of the associated diagnostic data.

20. The medical data indexing system of claim 1, wherein the requester is a client computer process, providing the index image comprises sending the index image or a pointer to the index image to the client, the client selects a body part by sending a message to the system specifying the body part, and providing the associated diagnostic data comprises sending the associated diagnostic data or a pointer to the associated diagnostic data to the client.

21. The medical data indexing system of claim 1, wherein the patient record provided by the medical data indexing systems comprises a directed acyclic graph having nodes and edges, wherein the nodes correspond to pre-defined body part identifiers, the edges connect nodes that share a parent-child relationship, and each node corresponding to one of the target data parts is associated with the diagnostic data for that target data part.

22. The medical data indexing system of claim 1 wherein none of the diagnostic data associated with the target body parts is provided to the medical information system storing the diagnostic data by the medical data indexing system, and the medical information system storing the diagnostic data is not part of the medical data indexing system.

23. A medical data indexing system comprising a patient indexing server comprising:
   (a) a programmable computer processor;
   (b) a non-transitory computer-readable memory accessible by the computer processor;
   (c) software stored in the computer-readable memory, wherein when the software is executed by the computer processor, the software causes the computer processor to:
      (i) obtain electronic patient records for a plurality of patients via a computer network, each patient having a set of body parts, from one or more medical information systems, each medical information system being separate and distinct from, and designed and developed separately from, the medical data indexing system, the patient record for each patient comprising (1) a specification of one or more target body parts having diagnostic data associated therewith stored in one of the medical information systems, one or more of the target body parts being an affected target body part, each of whose associated diagnostic data indicates the existence of a medical condition associated with the affected target body part, and (2) the diagnostic data for each target body part, wherein one or more of the target body parts are internal body parts;
      (ii) analyze the patient records to determine which body parts are the target body parts;
      (iii) analyze the diagnostic data to determine which body parts are the affected target body parts and to identify the indicated medical conditions;
      (iv) for each patient, construct a patient index comprising a pre-defined set of body part identifiers by identifying one or more pre-defined body part identifiers corresponding to the specification of each of the target body parts identified by the medical data indexing system's analysis, and automatically associate the diagnostic data for each of the target body parts with the identified pre-defined target body part identifiers in the patient index, and associate the indicated medical condition with each affected target body part's identifier in the patient index; and
      (v) receive data retrieval requests from requestors, each request specifying a patient, and, for each request, provide the patient index corresponding to the specified patient to the requestor.

24. The medical data indexing system of claim 23 wherein the patient records for at least one patient are retrieved from at least two medical information systems via the computer network.

25. The medical data indexing system of claim 24, wherein the requestor is a patient visualization server, the patient visualization server comprising a computer processor running software that causes the computer processor to:
   a. receive an index image request from a client specifying a patient;
   b. send a data retrieval request to the patient indexing server to request a patient index for the specified patient, and receive the patient index for the specified patient from the patient indexing server;
   c. generate an index image depicting the body parts corresponding to a subset of the pre-defined set of body part identifiers in the patient index, and, if one or more target body parts in the patient index are depicted in the index image, automatically highlight a portion of the index image depicting the one or more target body parts, and if one or more affected target body parts are depicted in the index image then, for each depicted affected target body part, automatically highlight a portion of the index image depicting the depicted affected target body part in a manner differentiating it from other body parts; and
   d. send the index image to the client.

26. The medical data indexing system of claim 25, further comprising the patient visualization server.

27. The medical data indexing system of claim 26, wherein the software further causes the computer processor in the patient visualization server to:
   a. receive index image revision requests from the client, revise the index image according to each request, automatically highlight the target body parts depicted in the revised index images, and provide the revised index images to the client; and
   b. receive data retrieval requests from the client, each request specifying one of the target body parts, and, for each request, provide some or all of the diagnostic data associated with the specified target body part to the client.

28. The medical data indexing system of claim 24, wherein the body parts are depicted in the index image in relative positions corresponding to the relative positions of the body parts in the patient.

29. The medical data indexing system of claim 24, wherein the pre-defined set of body part identifiers is hierarchical, based on parent-child relationships between the body parts, and the patient index comprises a directed acyclic graph having nodes and edges, wherein the nodes correspond to pre-defined body part identifiers, the edges connect nodes that share a parent-child relationship, and each node corresponding to a particular target body part is associated with the diagnostic data for that particular target body part.

30. The medical data indexing system of claim 29, wherein the nodes contain addresses of, or pointers to, the associated diagnostic data.

31. The medical data indexing system of claim 29, wherein the directed acyclic graph is depicted in the index image, and the nodes with associated diagnostic data are highlighted.

32. The medical data indexing system of claim 23 wherein none of the diagnostic data associated with the target body parts is provided to the medical information system storing the diagnostic data by the medical data indexing system.

33. A method of indexing medical data by a computer system, the method comprising the steps of:
   a. Receiving a patient identifier specifying a patient from a requestor, the patient having a set of body parts;
   b. automatically retrieving and receiving from a medical information system an electronic patient record for the patient via a computer network, the medical information system being separate and distinct from, and designed and developed separately from, the computer system performing the method, the patient record comprising (1) a specification of one or more target body parts having diagnostic data associated therewith stored in one of the medical information systems, including one or more internal body parts, one or more of the target body parts being an affected target body part, each of whose associated diagnostic data indicates the existence of a medical condition associated with the affected target body part, and (2) the diagnostic data associated with each of the target body parts;

c. analyzing the patient record to determine which body parts are the target body parts;
d. analyzing the diagnostic data to determine which body parts are the affected target body parts and to identify the indicated medical conditions;
e. generating an index image depicting a set of the patient's body parts;
f. if one or more of the target body parts identified by the analysis of one of the patient record retrieved over the computer network from one of the medical information systems are depicted in the index image, automatically highlighting those target body parts in the index image;
g. if one or more affected target body parts are depicted in the index image then, for each depicted affected target body part, automatically highlighting the depicted affected target body part in a manner differentiating it from other body parts;
h. providing the index image to the requestor; and
i. if the requestor selects one of the highlighted target body parts, providing some or all of the associated diagnostic data to the requestor.

34. The method of claim 33 wherein patient records for at least one patient are retrieved from at least two medical information systems via the computer network.

35. A method of indexing medical data by a computer system, the method comprising the steps of:
a. receiving a data retrieval request from a requestor, the request specifying a patient;
b. automatically obtaining an electronic patient record for the patient from one or more medical information systems via a computer network, each medical information system being separate and distinct from, and designed and developed separately from, the computer system performing the method, the patient having a set of body parts, the patient record comprising (1) a specification of one or more target body parts having diagnostic data associated therewith stored in one of the medical information systems, including one or more internal body parts, one or more of the target body parts being an affected target body part, each of whose associated diagnostic data indicates the existence of a medical condition associated with the affected target body part, and (2) the diagnostic data for each target body part;
c. analyzing the patient record to determine which body parts are the target body parts;
d. analyzing the diagnostic data to determine which body parts are the affected target body parts and to identify the indicated medical conditions;
e. constructing a patient index comprising a pre-defined set of body part identifiers by identifying one or more pre-defined body part identifiers corresponding to the specification of each of the target body parts identified by the analysis of the patient record as having diagnostic data associated therewith stored in one of the medical information systems, and automatically associating the diagnostic data for each of the target body parts with the identified pre-defined target body part identifiers in the patient index, and associating the indicated medical condition with each affected target body part's identifier in the patient index; and
f. providing the patient index to the requestor.

36. The method of claim 35 wherein patient records for at least one patient are retrieved from at least two medical information systems via the computer network.

* * * * *